US00PP21400P2

(12) United States Plant Patent
Bergman

(10) Patent No.: US PP21,400 P2
(45) Date of Patent: Oct. 19, 2010

(54) ***CHRYSANTHEMUM* PLANT NAMED 'YOLAKE PLACID'**

(50) Latin Name: *Chrysanthemum×morifolium*
Varietal Denomination: Yolake Placid

(75) Inventor: Wendy Bergman, Lehigh Acres, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/586,573

(22) Filed: Sep. 24, 2009

(51) Int. Cl.
*A01H 5/00* (2006.01)

(52) U.S. Cl. ..... Plt./297

(58) Field of Classification Search ..... Plt./297
See application file for complete search history.

*Primary Examiner*—Annette H Para
(74) *Attorney, Agent, or Firm*—S. Matthew Edwards

(57) ABSTRACT

A new *Chrysanthemum* plant named 'Yolake Placid,' particularly distinguished by the decorative-type flowers; white with a blush of lavender-pink ray florets; uniform growth habit with strong stems; early flowering response with excellent shelf life.

1 Drawing Sheet

Latin name of the genus and species of the plant claimed: *Chrysanthemum×morifolium.*

Varietal denomination: 'Yolake Placid'.

BACKGROUND OF THE NEW PLANT

The present invention comprises a new *Chrysanthemum*, botanically known as *Chrysanthemum×morifolium*, and hereinafter referred to by the variety name 'Yolake Placid'.

'Yolake Placid' is a product of a planned breeding program. The new cultivar has decorative-type flowers; white with a blush of lavender-pink ray florets; uniform growth habit with strong stems; early flowering response with excellent shelf life.

'Yolake Placid' originated from a hybridization made in February 2003 in a controlled breeding environment in Salinas, Calif. The female parent was a plant designated 'YB-A3813,' proprietary, unpatented, with slightly smaller flower size, similar flower color, and very vigorous growth habit.

The male parent of 'Yolake Placid' is identified as 'YB-A3951', proprietary, unpatented with medium pink flower color and semi-double flower form.

'Yolake Placid' was selected as one flowering plant within the progeny of the stated cross in November 2004, grown outdoors in a field covered with saran in Fort Myers, Fla.

The first act of asexual reproduction of 'Yolake Placid' was accomplished when vegetative cuttings were propagated from the initial selection in February 2005, in a controlled environment in Fort Myers, Fla.

A Plant Breeder's Right for this cultivar was applied for in Canada in October 2008. 'Yolake Placid' has not been made publicly available more than one year prior to the filing of this application.

BRIEF SUMMARY OF INVENTION

Horticultural examination of plants grown from cuttings of the plant initiated in February 2005, and continuing thereafter, has demonstrated that the combination of characteristics as herein disclosed for 'Yolake Placid' are firmly fixed and are retained through successive generations of asexual reproduction.

'Yolake Placid' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Yolake Placid' with colors being as true as possible with an illustration of this type. The photographic drawing shows four flowering potted plants of the new variety growing in a 5 inch pot, and a close-up of the flowers.

DETAILED BOTANICAL DESCRIPTION

The plant descriptions, measurements and aforementioned photographs were taken in Salinas, Calif. in April 2009 under greenhouse conditions. These plants were started and grown in central coastal California, then shipped to Gilroy in April 2009. Plants were grown under conditions which approximate those generally used in commercial potted *chrysanthemum* production and were about 9 weeks of age.

Color references are made to The Royal Horticultural Society Colour Chart (R.H.S.) 2001.

TABLE 1

DIFFERENCES BETWEEN THE NEW VARIETY 'YOLAKE PLACID' AND A SIMILAR VARIETY

| | 'Yolake Placid' | 'Yonew York' (U.S. Plant Pat. No. 15,698 |
|---|---|---|
| Ray floret color: | White with pink overlay | White with pink-purple overlay |
| Foliage color: | Darker | Somewhat lighter |
| Petiole length: | Shorter | Longer |
| Stem strength | Strong | Moderately strong |

Plant:
*Form, growth and habit.*—Herbaceous pot-type; spreading growth habit, freely branching. Suitable for production-center budded or no bud removal.
*Plant height.*—18-22 cm.
*Plant height (inflorescence included).*—22-25 cm.
*Plant width.*—18-20 cm.
Roots:
*Number of days to initiate roots.*—4 days at about 22 degrees C.
*Number of days to produce a rooted cutting.*—10 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—About RHS 147A.
*Lower surface.*—Closest to RHS 147B.
*Mature, leaf color, upper surface.*—Slightly lighter than RHS 147A.
*Lower surface.*—Closest to RHS 147B.
*Length.*—6.5-7.5 cm.
*Width.*—4.5-5.3 cm.
*Shape.*—Ovate.
*Base shape.*—Attenuate.
*Apex shape.*—Mucronulate.
*Margin.*—Palmately lobed; slightly serrate.
*Texture, upper surface.*—Bi-fid T-shaped hairs.
*Lower surface.*—Bi-fid T-shaped hairs.
*Color of veins, upper surface.*—RHS 144B.
*Color of veins, lower surface.*—RHS 144C.
*Petiole color.*—RHS 144B.
*Length.*—1.0 cm.
*Diameter.*—0.2-0.25 cm.
*Texture.*—Bi-fid T-shaped hairs.
Stem:
*Quantity of main branches per plant.*—3-5.
*Quantity of leaves per branch.*—8-12.
*Color of stem.*—RHS 146B.
*Length of stem.*—17-20 cm.
*Diameter.*—0.5-0.7 cm.
*Length of internodes.*—0.5-1.8 cm.
*Texture.*—Bi-fid T-shaped hairs.
*Color of peduncle.*—RHS 146C.
*Length of peduncle.*—2.8-5.0 cm.
*Peduncle diameter.*—0.2 cm.
*Texture.*—Bi-fid T-shaped hairs.
Inflorescence:
*Type.*—Compositae type, solitary inflorescences (decorative-type) borne terminally above foliage, ray florets arranged acropetally on a capitulum.
*Quantity of short days to flowering (response time).*—51-55 days.
*Quantity of inflorescences per plant.*—About 10-12.
*Lastingness of individual blooms on the plant.*—About 36 days.
*Fragrance.*—Moderate.
Bud (just before opening/showing color):
*Color.*—RHS N155B but with a little more pink.
*Length.*—0.8-1.3 cm.
*Width.*—1-1.2 cm.
*Shape.*—Oblate.
Immature inflorescence:
*Diameter.*—4.5-5.0 cm.
*Color of ray florets, upper surface.*—RHS N155B but with little more pink; RHS 72B margins.
*Lower surface.*—RHS N155B but with a little more pink.
Mature inflorescence:
*Diameter.*—7-7.3 cm.
*Total diameter of 'disc'.*—0.4-0.5 cm only found on very mature inflorescences.
Ray florets:
*Average quantity of florets.*—140-150.
*Color of florets, upper surface.*—Closer to RHS N155B; sometimes with a hint of RHS N74C at margins and apex.
Lower surface.—RHS N155B with pink suffusion of RHS 77C to RHS 77D in the middle.
*Length.*—2.7-3.1 cm.
*Width.*—0.7-1.0 cm.
*Shape.*—Elliptical.
*Apex shape.*—Praemorse.
*Margin.*—Entire.
*Texture, upper surface.*—Papillose.
*Lower surface.*—Papillose.
Disc florets:
*Average quantity of florets.*—35-40.
*Color of florets.*—RHS 14A at apex; RHS 1D basally.
*Length.*—0.5 cm.
*Width.*—0.1 cm.
*Shape.*—Tubular, enlongated.
*Apex shape.*—Acute, 5 pointed.
Phyllaries:
*Quantity.*—17-20.
*Color, upper surface.*—RHS 147B; lighter at margins.
*Lower surface.*—RHS 147B; lighter at margins.
*Length.*—0.6-0.7 cm.
*Width.*—0.2 cm.
*Shape.*—Lanceolate.
*Apex shape.*—Acute.
*Based.*—Fused.
*Margins.*—Entire; papery and opaque.
*Texture, upper surface.*—Glossy and smooth.
*Lower surface.*—Bi-fid T-shaped hairs.
Reproductive organs:
*Pistil.*—1.
*Length.*—0.5-0.6 cm.
*Style color.*—RHS 1C.
*Style length.*—0.3-0.4 cm.
*Stigma color.*—RHS 1B.
*Stigma shape.*—Bi-parted.
*Stamens.*—4.
*Color of filaments.*—RHS 1C.
*Length filaments.*—0.2 cm.
*Anther color.*—RHS 12C.
*Anther length.*—0.2 cm.
*Anther shape.*—Oblong.
*Color of pollen.*—RHS 16A.
*Pollen amount.*—Scarce.
*Fertility/seed set.*—Has not been observed on this hybrid.
Disease/pest resistance: Disease resistance or susceptibility has not been observed on this hybrid.

What is claimed is:

1. A new and distinct variety of *Chrysanthemum* plant named 'Yolake Placid,' substantially as illustrated and described herein.

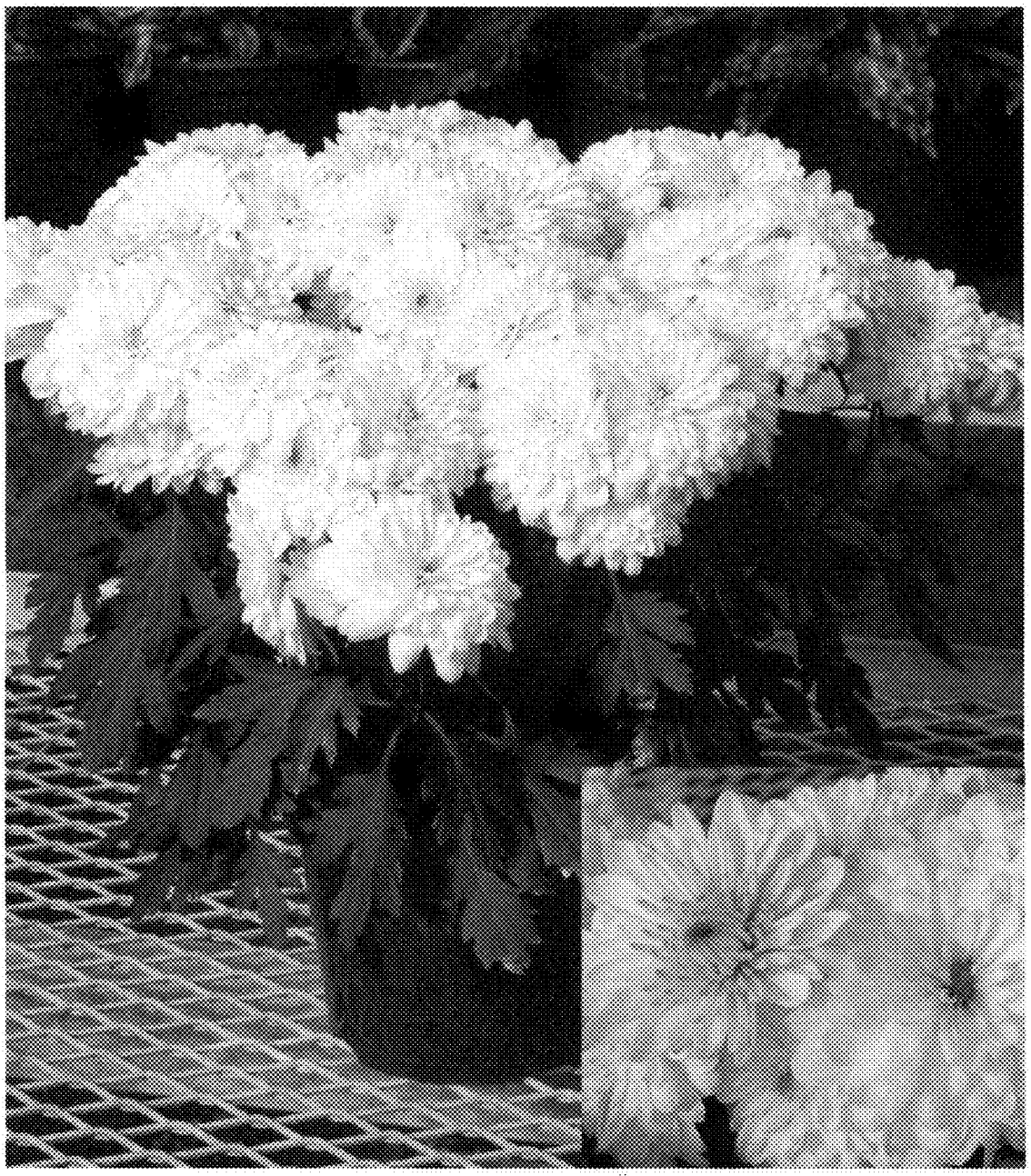

* * * * *